United States Patent
Crichfield et al.

(10) Patent No.: US 6,617,451 B1
(45) Date of Patent: Sep. 9, 2003

(54) ENANTIOSELECTIVE ACYLATION OF CIS RACEMIC AZETIDINONES

(75) Inventors: Kathy Sue Crichfield, Bloomingdale, IN (US); John Eric Hart, Saint Bernice, IN (US); Radhe Krishan Vaid, West Lafayette, IN (US); Daniel Edward Verral, Midland, MI (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/018,187

(22) PCT Filed: Jul. 7, 2000

(86) PCT No.: PCT/US00/16314

§ 371 (c)(1),
(2), (4) Date: Dec. 13, 2001

(87) PCT Pub. No.: WO01/07438

PCT Pub. Date: Feb. 1, 2001

Related U.S. Application Data

(60) Provisional application No. 60/145,434, filed on Jul. 23, 1999.

(51) Int. Cl.[7] .................. C07D 205/085; C07D 405/06; C12P 17/16
(52) U.S. Cl. ........................ 540/355; 540/364; 435/118; 435/121
(58) Field of Search ................. 435/118, 121; 540/355, 364

(56) References Cited

U.S. PATENT DOCUMENTS

| | | | |
|---|---|---|---|
| 5,037,976 A | * | 8/1991 | Fujii et al. ................. 540/300 |
| 5,057,607 A | | 10/1991 | Zmijewski et al. |
| 5,142,038 A | * | 8/1992 | Doecke et al. .............. 540/200 |

FOREIGN PATENT DOCUMENTS

| | | | |
|---|---|---|---|
| EP | 365 212 A | | 4/1990 |
| EP | 634 492 A | | 1/1995 |
| WO | WO 9602630 A1 | * | 2/1996 ............ C12N/1/21 |

OTHER PUBLICATIONS

Doecke, Snythesis 985, 1991.*

Milton J. Zmijewski, Jr., et al., *Tetrahedron Letters*, 32:13, 1621–1622 (1991); Enantioselective Acylation of a Beta–Lactam Intermediate in the Synthesis of Loracerbef Using Penicillin G Amidase.

Minoru Hatanaka, et al., *Tetrahedron Letters*, 24:44, 4837–4838 (1983); A Simple Synthesis of (±)–1–Carbacephem Derivatives.

* cited by examiner

*Primary Examiner*—Mark L. Berch
(74) *Attorney, Agent, or Firm*—Tina M. Tucker

(57) ABSTRACT

Cis-β-lactam compounds having structure (II) are described herein which are prepared by enantioselective acylation of the free amine in the presence of Penicillin G Amidase.

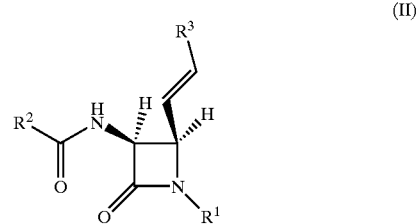

(II)

4 Claims, No Drawings

ENANTIOSELECTIVE ACYLATION OF CIS RACEMIC AZETIDINONES

This application claims the benefit of the provisional application U.S. Ser. No. 60/145,434, filed Jul. 23, 1999.

FIELD OF THE INVENTION

The present invention relates to chiral cis-azetidinones having an unsaturated side-chain prepared by enantioselective acylation of a monocyclic β-lactam with Penicillin G Amidase.

BACKGROUND OF THE INVENTION

Non-classical β-lactams such as the monobactams (e.g., aztreonam), carbapenems (e.g., thienamycin), and carbacephems (e.g., loracarbef) have been shown to be clinically effective anti-bacterial agents. Much attention has been focussed on the development of economical, large scale synthesis of these derivatives. Since loracarbef is available only via a total synthesis, improvements in the manufacturing process are of particular interest. One of the most challenging synthetic steps is the resolution of the chiral cis-β-lactam intermediates. U.S. Pat. No. 5,057,607 provides a enantiomerically selective biocatalyzed acylation of a racemic mixture of cis-3-amino-2-[2-(2-furanyl)ethyl]-4-oxo-1-azetidine acetic acid (or its alkyl ester) with methyl phenylacetate (or methyl phenoxyacetate) in the presence of a penicillin G amidase enzyme. The racemic materials serve as the substrate for the enzyme. Once acylated, the acylated active enantiomer is isolated and the inactive enantiomer is disposed of thus reducing the overall yield of the intermediate. Therefore, there is a need for a means of producing the desired enantiomeric cis-β-lactam intermediate with higher overall yields.

BRIEF SUMMARY OF THE INVENTION

The present invention provides a cis-β-lactam compound having structure II and a process for preparing the cis-β-lactam compound having structure II:

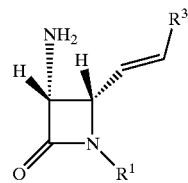

II where $R^1$ is $-SO_3^-$, $-SO_3(C_1-C_4)$alkyl, $-CH_2CO_2H$, or $-CH_2CO_2R^{1'}$, where $R^{1'}$ is $(C_1-C_4)$alkyl, benzyl, or substituted benzyl (e.g., p-nitrophenylmethylene); $R^2$ is benzyl or phenoxymethylene; and $R^3$ is 2-furyl, phenyl, or 2-methoxyphenyl. In a preferred embodiment, $R^1$ is $-CH_2CO_2H$ or an ester thereof. Compound II is prepared by the steps of (i) providing a racemic mixture of cis-azetidinones having structures Ia and Ib

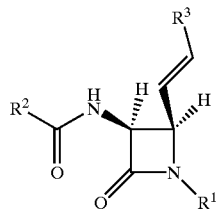

Ia

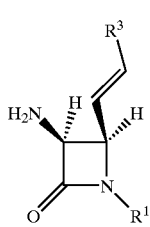

Ib where $R^1$ and $R^3$ have the same meaning as above, and (ii) reacting the racemic mixture with a $(C_1-C_4)$alkyl phenylacetate or a $(C_1-C_4)$alkyl phenoxyacetate in the presence of penicillin G amidase. Once acylated, Compound II may be further modified. For example, Compound II may be hydrogenated to form a compound having a saturated sidechain (Compound III below).

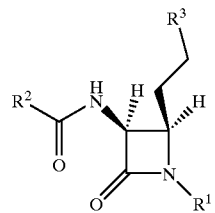

III

DEFINITIONS

As used herein, the term "$(C_1-C_4)$alkyl" refers to an alkyl group having one to four carbon atoms (e.g., methyl, ethyl, propyl and butyl). The alkyl group may be a straight or branched chain (e.g., n-propyl, i-propyl, n-butyl, i-butyl, s-butyl, and t-butyl)

DETAILED DESCRIPTION OF THE INVENTION

The use of Penicillin G Amidase for the enzymatic acylation of β-lactam antibiotics and resolution of cis racemic azetidinones has been previously reported. (see, e.g., U.S. Pat. No. 5,057,607, incorporated herein by reference; Zmijewski Jr., M. J., et al., "Enantioselective acylation of a Beta-Lactam Intermediate in the synthesis of Loracarbef using Penicillin G Amidase," *Tetrahedron Letters*, 32(13), 1621–1622 (1991); and Briggs, B. S., et al., "Side Chain Selectivity and Kinetics of Penicillin G Amidase in Acylating a Cis-Racemic β-Lactam Intermediate in the Synthesis of Loracarbef," *New J. Chem.*, 18, 425–434 (1994).) However, none of the previous investigators realized the utility and advantages of enantioselectively acylating a cis-β-lactam intermediate having an unsaturation in the side chain. Since enzymes are very substrate sensitive, it was also unknown until the discovery by the Applicants that one could enantioselectively acylate a cis-β-lactam intermediate having an unsaturation in the side chain in the presence of Pencillin G Amidase.

The presence of the unsaturation in the side-chain provides several advantages that cannot be realized in the previously disclosed hydrogenated intermediate. For example, one may be able to recycle the undesired inactive cis-enantiomer by racemizing the unwanted cis-isomer. Scheme I below illustrates a potential means of providing this racemization and subsequent enantioselective acylation to increase the overall yield of the desired cis-enantiomer.

Scheme I

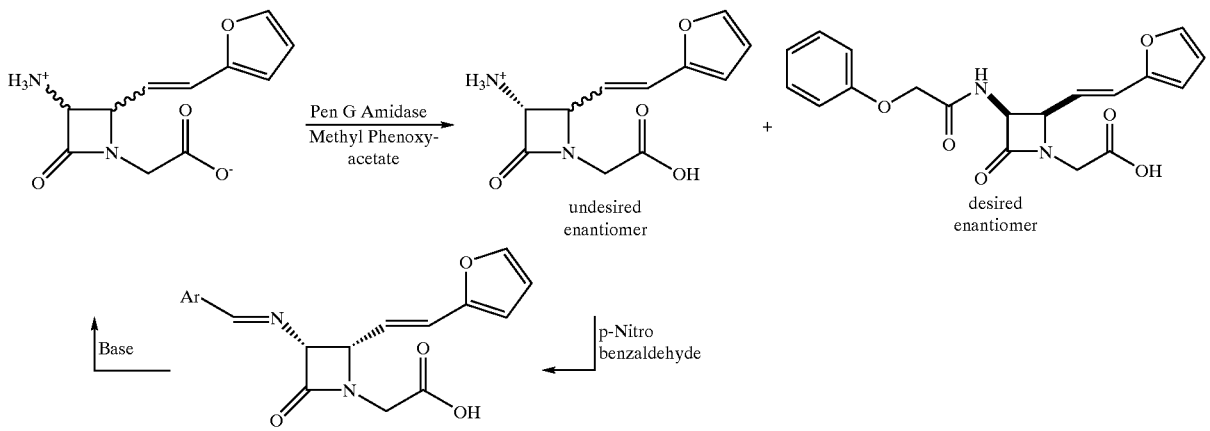

Applicants have observed that when the methyl ester of cis-3-amino-2-[trans-2-(2-furanyl)ethylene]-4-oxo-1-azetidineacetic acid is converted to its 3-p-nitrobenzyl imine derivative under basic conditions epimerization of the C-3 stereocenter occurs. Other substituents located alpha to the C-3 and/or C-2 stereocenters have also been shown to activate azetidinones towards racemization. (see, e.g., Alcaide, B., et al., *Tetrahedron Letters*, 39, 5865–5866 (1998); Suarato, A., et al, *Tetrahedron Letters*, 42, 4059–4062 (1978); and Kametani, T., et al, *Heterocycles*, 16(4), 539–547 (1981)). Therefore, it is reasonable to believe that treatment with base will epimerize the two chiral centers thus providing a means for recovering additional desired enantiomer. Suitable bases include organic bases (e.g., trialkyl amines, pyridines, pyrimidines, quinolines, isoquinolines and derivatives thereof), metal alkoxides, diazabicyclo[5.4.0]undec-7-ene (DBU). Generally, the reaction is run in a non-nucleophilic solvent (e.g., methylene chloride, ethers, hydrocarbons, benzene and toluene) at about −35° C. to about 70° C.

The presence of the unsaturation in the azetidinone also provides a reactive site for derivatization. For example, the unsaturated side-chain may be converted to a methyl group. (see Scheme II) Cleavage of an unsaturation to produce an alkyl group is well known to those skilled in the art. The enantioselective acylation followed by conversion of the unsaturated side-chain could provide an alternative method for making enantiomerically pure intermediates in the synthesis of monobactams (e.g., Azetreonam).

Scheme II

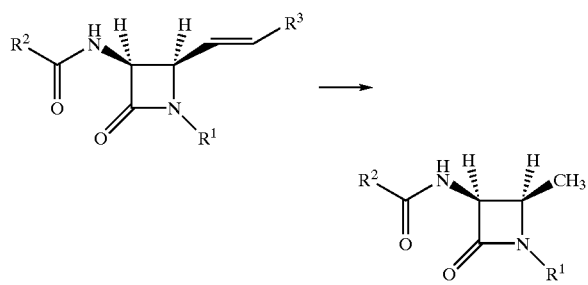

Alternatively, one could oxidatively cleave the unsaturation to provide a carboxyl or aldehyde group at the 2 position of the β-lactam ring. The oxidized product could then be derivatized to provide a variety of intermediates that could be used in the development of new antibiotic agents.

The racemic mixture of cis-β-lactams can be obtained by methodology well-known to those skilled in the β-lactam art. For example, the cis-β-lactam racemates may be produced using the ketene/imine (2+2) cycloaddition reaction described in Hatanaka, et al., *Tetrahedron Letters*, 24(44), pp. 4837–4838 (1983); Georg, F. I. and V. T. Ravikumar, The Organic Chemistry of β-Lactams, Chapter 6, G.I. Georg (Ed.), VCH, pp 295–368 (1993); and U.S. Pat. Nos. 4,260,743 and 5,159,073, both incorporated herein by reference. A preferred method utilizes the formation of a "Dane salts" which is formed by allowing a solution of a potassium salt of an α-amino acid to react with a β-dicarbonyl compound. The Dane salt is then reacted with ethyl chloroformate and, triethylamine to form a mixed anhydride which is then reacted in situ with a Schiff base to afford the cis-isomer stereoselectively. For a more detailed description, see the preparation section of the Examples.

The term "penicillin G amidase" (or the alternative term "penicillin G acylase") is well-known in the β-lactam art as an enzyme which catalyzes the hydrolysis of the penicillin G sidechain(phenylacetyl) from penicillin substrates. Penicillin G amidases suitable for use in the process of the present invention may be isolated by known methodology from many organisms, for example, *E. coli, B. megaterium, Ps. melanogenum, K. citrophila*, and *P. rettgei*. In this regard Schlwale and Sivarawan, Process Biochemistry, August., 1989, pp. 146–154 sets forth a review of the state of the art of penicillin G amidase (acylase) production and application. Penicillin G amidase isolated from *E. coli* is preferred.

Once isolated, the penicillin G amidase may be used in "free" form, i.e., solubilized in aqueous or substantially aqueous solutions, or may be immobilized onto a support matrix such as an intermolecular adduct with glutaraldehyde; Sepharoses; Sephadex G-200™, acrylamide, N,N-methylenebis (acrylamide) and maleic anhydride; Dextran™; maleic anhydride; tetramethyleneglycol; dimethacrylate; methacrylic acid, DEAE-Cellulose™; CM-Cellulose™; AE-Cellulose™; and other cellulose derivatives; CM-Sephadex Amberlite IRC-50™. and other weak cation and anion exchangers; ethylene maleic anhydride copolymers; Nylon™; Amberlite XAD-7™; Sucrose/epichlorohydrin copolymer; polyacrylamide; cellulose; intermolecular adduct with glutaraldehyde; acrylamide copolymer; anion exchange phenol-formaldehyde resin;

DEAE-Sephadex™; glycidyl methacrylate; methylene bisacrylamide; diatomaceous earth; poly(hydroxyethyl methacrylate); Eupergit C™; basic anion exchanger (polyamine; styrene; divinylbenzene); cellulose triacetate fibres; AH-Sepharose™/benzoquinone; nitrocellulose fibres; a polyethylene imine; Bentonite™; a polyacrylamide gel entrapment or derivatised polyacrylonitrile.

The immobilized penicillin G amidase may be obtained commercially. For example, the immobilized enzyme used in the experimental section below was obtained from SCLAVO S.p.A.—Biochemical Division De. Bi., S. S. Podana Superiore, Km. 160,20060—Cassina de Pecchi—Milan, Italy. It is believed that any penicillin G amidase enzyme will be efficacious as a biocatalyst in the present invention whether used in free form or immobilized on a support matrix; however, it is preferred that the enzyme be immobilized on a solid support matrix, because such catalysts can be used several times. For example, when the reaction is deemed complete, the immobilized enzyme may simply be filtered away from the reaction mixture, washed with deionized water, stored in glycerol/water under an inert atmosphere such as nitrogen or argon at reduced temperature, for example at about 4° C., and re-used.

The substrate is preferably present in the reaction mixture in a concentration of 0.1% (w/w) to about 20% (w/w) although concentration is not critical to the operability of the process. The amount of penicillin G amidase present in the reaction mixture dictates the rate of reaction, because it serves as a biocatalyst. A concentration of from about 10 I.U./g substrate (i.e., the β-lactam of formula (2)), to about 125 I.U./g substrate of penicillin G amidase is preferred. More preferably, the concentration will be at the lower end of the foregoing range, i.e., from about 10 I.U./g substrate to about 30 I.U./g substrate, and, most preferably, from about 15 I.U./g substrate to about 25 I.U./g. In the context it is used herein, one international unit (I.U.) is the amount of enzyme that will catalyze hydrolysis of one μmole of penicillin G in one minute at 28° C.

The acylation reaction of the present invention may be carried out in aqueous media at a pH of about 5 to about 8, preferably at about pH=6, thus providing an environmentally-compatible synthesis of intermediates useful in the synthesis of 1-carba(dethia)3-cephems which is suitable for use in large scale synthesis. Alternatively, the reaction may be carried out in a water/water-miscible polar organic solvent mixture comprising from about 1 to about 28% of a polar organic solvent such as acetone, tetrahydrofuran, propylene glycol methyl ether, propylene glycol, ethylene glycol dimethyl ether, 2-methoxyethyl ether, ethylene glycol, or glycerol, and from about 99% to about 72% water.

The temperature at which the process may be carried out will be appreciated by one of ordinary skill in enzyme catalysis and thus is not a critical limitation of the process; however, a temperature range of about 10° C. to about 45° C. is preferred. A more preferred temperature is about 28° C.

Once acylated, the vinyl side-chain may be hydrogenated. A standard hydrogenation is accomplished in the presence of a hydrogenation catalyst and a solvent, such as methylene chloride, dimethylformamide, ethers, esters and mixtures thereof. Suitable hydrogenation catalysts include nickel, platinum, rhodium, ruthenium, copper chromite, iridium, osmium, palladium, and combinations thereof. A preferred catalyst is a supported palladium, e.g., 5% or 10% palladium on carbon, barium carbonate, or other suitable support. The reduction generally is carried out at atmospheric conditions or at somewhat elevated pressures, and at substantially room temperature.

The following examples serve to illustrate the synthesis of enantiomeric β-lactam compounds which may be useful intermediates in the synthesis of existing antibiotic agents (e.g., loracarbef known under the tradename Lorabid™ available from Eli Lilly and Company) and the development of new antibiotic agents. Although the following examples exemplify the inventive enantioselective acylation process for the preparation of compounds where $R^1$ is —$CH_2CO_2H$ or an ester thereof (e.g., —$CH_2CO_2R^1$), one skilled in the art can easily adapt the process for the preparation of compounds where $R^1$ is —$SO_3$— or —$SO_3(C_1$–$C_4)$ alkyl using the appropriate starting materials and the general procedures detailed below.

EXAMPLES

The following abbreviations are used through out the examples to represent the respective listed materials:

MPA=methyl phenylacetate

MPOA=methyl phenoxyacetate

Penicillin G Amidase impregnated on polyacrylamide beads was purchased from Recordati S.p.A. and characterized as follows: the enzyme beads were washed with deionized water and each preparation assayed prior to use. Enzyme activity was determined by measuring the rate of enzymatic hydrolysis of Penicillin G. One international unit (I.U.) of enzyme corresponds to the quantity of Penicillin G Amidase needed to hydrolyze 1 μmol of Penicillin G in 1 minute at 28° C. and a pH of 8, as determined by titration of the phenylacetic acid produced in the reaction.

All melting points are uncorrected. $^1$H NMR and $^{13}$C NMR spectra were recorded at 300 MHz on a Broker™ DPX-300 in DMSO-d6 unless otherwise stated. IR spectra were recorded on a Nicolet™ 510P as KBr pellets. Mass spectra were obtained by Flow Injection Analysis on a Micromass™ QTOF Mass Spectrometer. Optical rotations were recorded at ambient temperature and 589 nm on a Perkin-Elmer™ Model 341 using methanol as the solvent.

Chiral HPLC analyses were carried out on a Shimadzu Chromatography System with a diode array detector using a Chiralcol™ OD (4.6×250 mm) column. Free acid substrates were converted to the methyl ester using diazomethane before being eluted under isocratic conditions (flow 1.0 ml/min.) with a 30% IPA in heptane solvent mixture.

Preparations

General Preparation for Enamines A, B and C

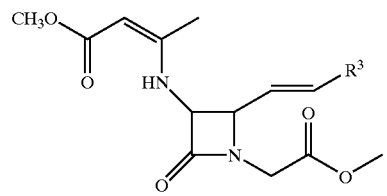

A: $R^3$ = 2-furyl
B: $R^3$ = phenyl
C: $R^3$ = 2-methoxyphenyl

Methyl aminoacetate: Methylene chloride (3,740 ml) was added to a 5-Liter 3-necked round bottom flask equipped with an overhead stirrer, vent hose connected to a bubbler, a thermometer, and an ammonia inlet. After cooling to +10° C, methyl aminoacetate hydrochloride (462 g, 3.68 mol) was added. Keeping the temperature at +10° C., anhydrous ammonia was added to the reaction until gas uptake ceased.

The endpoint was determined by an increase in gas production through the bubbler. After the addition, the contents were stirred at +10° C. for an additional 15 minutes before removing the solids by vacuum filtration and washing them with 540 ml of cold methylene chloride. The filtrate was vacuum distilled to a volume of 3,040 ml at +10° C.

Schiff base: Methyl aminoacetate (1.05 equivalents per equivalent aldehyde) was added to a 1-liter 3-necked round bottom flask, equipped with an overhead stirrer, thermometer, and nitrogen inlet. The solution was stirred and cooled to 3° C. Silica gel was added followed immediately by the addition of the requisite aldehyde; 3-(2-furyl) acrolein, trans cinnamaldahyde, or 2-methoxycinnamaldehyde. The reaction was stirred under nitrogen at 7° C. for 4–5 hours. The contents were then cooled to −10° C. over 35 minutes and held at −10° C. for 45 minutes. The solids were removed by vacuum filtration and washed with cold methylene chloride. The filtrate was kept at a temperature below 0° C.

To a 1-liter 4-necked round bottom flask, equipped with a thermometer, mechanical stirrer, and two dropping funnels, was added Glycine Dane salt (1.2 equivalents per equivalent Schiff base), methylene chloride (10–20 ml per g aldehyde), and triethylamine (2.4 equivalents per equivalent Schiff base). This mixture was stirred at 0–3° C. for 15 minutes. Ethyl chloroformate (2.3 equivalents per equivalent Schiff base) was slowly added via a dropping funnel while simultaneously adding a methylene chloride solution of Schiff base. The internal reaction temperature was maintained at 0–7° C. during the additions. After the complete add, the reaction was stirred at 3–7° C. for 3–6 hours before adding deionized (DI) water. While maintaining the temperature at 13–17° C., the reaction pH was adjusted to 5.7–6.2 with concentrated HCl. The organic layer was separated and the aqueous layer washed with additional methylene chloride. The organic layer was dried over anhydrous $Na_2SO_4$ and concentrated at reduced pressure to produce Enamine A, B or C.

Preparation of Methyl cis-3-Ammonium-2-[trans-2-(2-furanyl)ethylene]-4-oxo-1-azetidineacetate Oxalate Salt (1a)

To a 3-neck flask equipped with a thermometer, condenser and mechanical stirrer was added 700 ml of methylene chloride solution containing 45 g of Enamine A. The contents were heated to reflux at 38–42° C. A methanol solution of oxalic acid (21.6 g) was added over 75 minutes using a drop funnel. Ethyl acetate 500 ml was added to the reaction mixture. The contents were stirred for 15 minutes. The slurry obtained was filtered and washed with 200 ml of EtOAc. Thus, 29.6 g of 1a was obtained after drying in a vacuum oven at 30° C. Re-crystallization may be performed using methanol and acetonitrile. M.p. of 1a=152–154° C. $^1$H NMR (DMSO-$d_6$) δ: 3.7 (s, 3H), 3.8 (d, 1H), 4.1 (d, 1H), 4.5 (dd, 1H), 4.6 (dd, 1H), 6.1 (dd, 1H), 6.5 (m, 2H), 6.6 (d, 1H), 7.7 (s, 1H), 8.2 (br, 3H).

Preparations of Zwitterions cis-3-Amino-2-[trans-2-(2-furanyl)ethylene]-4-oxo-1-azetidineacetic Acid (2a) cis-3-Amino-2-(trans-2-phenylethylene)-4-oxo-1-azetidine Acetic Acid (2b); And cis-3-Amino-2-[trans-2-(2-methoxyphenyl)ethylene]-4-oxo-1-azetidine Acetic Acid (2c)

Enamine A, B or C prepared above in methylene chloride was charged to a 500 ml round bottom flask and cooled to −5° C. Methanesulfonic acid (70%) was added and the reaction allowed to exotherm to −2° C. The reaction was stirred for 2 hours before being warmed to 7° C. and DI water added. The aqueous layer was separated and additional cold DI water added to the organic layer. Again the aqueous layer was separated and combined with the first. The combined aqueous layer was adjusted to pH=10.0 with 50% NaOH and stirred for 15–60 minutes to ensure a stable pH before storing cold for future use.

cis 3-Amino-2-[2-(2-furanyl)ethylene]-4-oxo-1-azetidine Acetic Acid (2a)

The solid zwitterion was isolated by precipitation from the aqueous layer upon adjustment to pH 5.5 with concentrated HCl at −3° C. The solid was washed with a minimum of ice cold water before drying overnight under house vacuum at +30° C. Isolated Yield=66%; M.p.=248° C.; IR (KBr cm$^{-1}$): 1654, 1767, 3477. $^1$H NMR (DMSO-d6) δ: 7.62 (1H, d), 6.48 (3H, m), 6.14 (1H, dd), 4.98 (3H, br), 4.36 (2H, m), 3.98 (1H, d), 3.56 (1H, d). $^{13}$C NMR (DMSO-d6) δ: 41.61, 60.68, 63.68, 108.96, 111.65, 123.01, 123.47, 142.82, 151.71, 169.13, 169.75. MS (FD): m/e 237.2 (FW 236.2).

cis 3-Amino-2-(2-phenylethylene)-4-oxo-1-azetidine Acetic Acid (2b)

The solid zwitterion was isolated as before. Isolated Yield=62%; m.p.=240° C.; IR (KBr cm$^{-1}$): 1650, 1769, 3496. $^1$H NMR (DMSO-d6) δ: 7.40 (5H, m), 6.74 (1H, d), 6.38 (1H, dd), 4.92 (3H, br), 4.36 (2H, m), 3.94 (1H, d), 3.58 (1H, d). $^{13}$C NMR (DMSO-d6) δ: 41.50, 61.04, 63.86, 125.30, 126.53, 127.81, 128.52, 134.99, 136.32, 169.41, 169.78. MS (FD): m/e 247.3 (FW 246.3).

cis 3-Amino-2-[2-(2-methoxyphenyl)ethylene]-4-oxo-1-azetidine Acetic Acid (2c)

The solid zwitterion was isolated as before. Isolated Yield=52%; m.p.=238° C.; IR (KBr cm$^{-1}$): 1646, 1772, 3480. $^1$H NMR (DMSO-d6) δ: 7.56 (1H, d), 7.26 (1H, m), 6.94 (3H, m), 6.34 (1H, dd), 5.14 (3H, br), 4.38 (2H, m), 3.98 (1H, d), 3.78 (3H, s), 3.56 (1H, d). $^{13}$C NMR (DMSO-d6) δ: 41.52, 55.38, 61.38, 63.61, 111.30, 120.40, 124.74, 125.33, 126.73, 129.20, 129.57, 156.15, 169.16, 169.78. MS (FD): m/e 277.2 (FW 276.3).

Alternatively, the zwitterions 2a, 2b and 2c may be prepared by the basic hydrolysis of the corresponding oxalate salt of the methyl ester. The following describes the preparation of 2a; however, the same general procedure may be used in the preparation of 2b and 2c. To a solution of methyl ester (1a) in water, was added 50% aqueous NaOH to a pH of about 11. After stirring at room temperature for 20–30 minutes, the slurry was filtered to remove the sodium oxalate salt. The filtrate was stirred at room temperature for an additional 30 minutes before cooling to 0° C. and adjusting the pH to 5.0 using concentrated hydrochloric acid solution. The resulting slurry was stirred for 1 hour at 0° C. before isolating the zwitterion 2a by vacuum filtration and drying overnight under vacuum at 25° C.

Example 1

Preparation of Compounds (1):

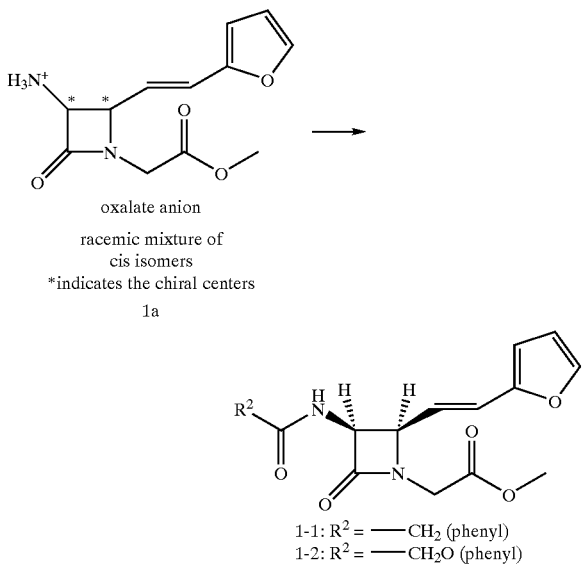

oxalate anion racemic mixture of
cis isomers
*indicates the chiral centers
1a 1-1: $R^2 =$ ——$CH_2$ (phenyl)
1-2: $R^2 =$ ——$CH_2O$ (phenyl)

In a typical reaction, 1.68 mmol of compound 1a is dissolved in deionized water and the pH adjusted to 6.0 with ammonium hydroxide and phosphoric acid. Either 2.52 mmol of methyl phenoxyacetate or methyl phenylacetate is added to the mixture. Immobilized penicillin G amidase (34 international units (IU)) is added to start the reaction. During the reaction, the pH is maintained by the addition of 2.5 N ammonium hydroxide and the temperature is held at 28° C. Samples (100 μl) are pulled every 20 minutes and examined for products by HPLC. The product was isolated by extraction into organic media.

Methyl-3-(S)-phenylacetamido-2-(R)-[trans-2-(2-furanyl)ethylene]-4-oxo-1-azetidineacetate (Compound 1-1)

Isolated Yield=44% (88% of theory); m.p.=185° C.; IR (KBr cm$^{-1}$): 1653, 1740, 1780, 3288. $^1$H NMR (DMSO-d6) δ: 8.96 (1H, d), 7.72 (1H, s), 7.14 (4H, m), 6.54 (2H, m), 6.40 (1H, m), 6.12 (1H, dd), 5.28 (1H, dd, J=5.1 Hz), 4.48 (1H, m, J=5.1 Hz), 4.22 (1H, d), 3.92 (1H, d), 3.66 (3H, s), 3.40 (2H, d). $^{13}$C NMR (DMSO-d6) δ: 41.65, 41.94, 52.03, 59.92, 60.56, 109.39, 111.67, 122.09, 123.99, 126.20, 127.97, 128.77, 135.89, 143.14, 151.52, 166.48, 168.48, 170.38. MS (EI): m/e 367.1 (FW 368.39). Optical rotation: $[\alpha]_D$=78.34 (c 2, MeOH, 25° C.). e.e.=>95% Absolute configuration: (2R, 3S)

Methyl-3-(S)-phenoxyacetamido-2-(R)-[trans-2-(2-furanyl)ethylene]-4-oxo-1-azetidineacetate (Compound 1-2)

Isolated Yield=46% (92% of theory); m.p.=155–157° C.; IR (KBr cm$^{-1}$): 1690, 1750, 1769, 3290. $^1$H NMR (DMSO-d6) δ: 9.02 (1H, d), 7.68 (1H, s), 7.14 (2H, m), 6.86 (3H, m), 6.56 (2H, m), 6.46 (2H, m), 6.12 (1H, dd), 5.26 (1H, dd, J=5.1 Hz), 4.65–4.52 (3H, m), 4.16 (1H, d), 3.88 (1H, d), 3.66 (3H, s). $^{13}$C NMR (DMSO-d6) δ: 41.56, 52.03, 59.45, 60.91, 66.50, 109.51, 111.70, 114.50, 121.01, 121.78, 124.31, 129.24, 143.14, 151.48, 157.68, 166.16, 168.17, 168.46. MS (EI): m/e 383.3 (FW 384.39). Optical rotation: $[\alpha]_D$=28.74 (c 2, MeOH, 25° C.). e.e.=>95% Absolute configuration: (2R, 3S).

Example 2

Preparation of Compounds (2):

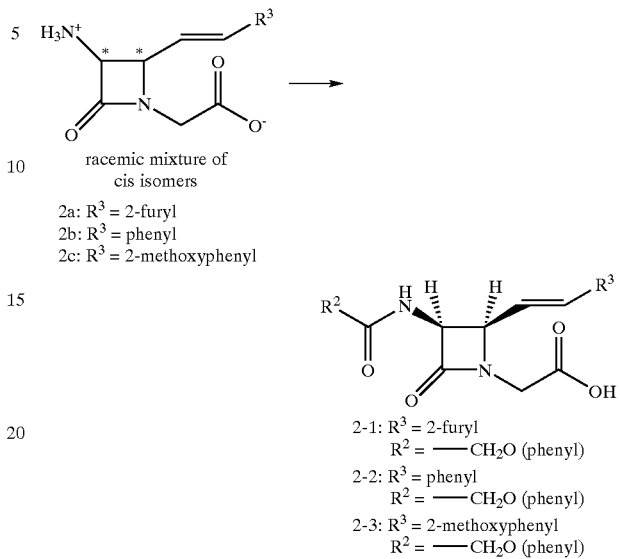

racemic mixture of
cis isomers

2a: $R^3$ = 2-furyl
2b: $R^3$ = phenyl
2c: $R^3$ = 2-methoxyphenyl 2-1: $R^3$ = 2-furyl
$R^2$ = ——$CH_2O$ (phenyl)
2-2: $R^3$ = phenyl
$R^2$ = ——$CH_2O$ (phenyl)
2-3: $R^3$ = 2-methoxyphenyl
$R^2$ = ——$CH_2O$ (phenyl)

Each of the compounds 2-1, 2-2, and 2-3 were prepared using the following general procedures.

Zwitterion 2a was dissolved in water (40–80 mg/ml) and the acidity adjusted to pH 6.2–6.6 with phosphoric acid (85%) while stirring at +28° C. The immobilized enzyme (20 I.U. per g of zwitterion 2a) was added, and the reaction started by the addition of methyl phenoxyacetate (0.62 eq. per zwitterion 2a). Ammonium hydroxide (6.5% aqueous solution) was used to maintain pH 6.2–6.6 during the reaction. The product formation was monitored using a titrometer. When the base consumption stopped (<0.1 ml NH$_4$OH added over 30 minutes), the enzyme was removed by vacuum filtration and the product precipitated by acidification to pH 2.5–1.8 using concentrated hydrochloric acid solution. The acylated product (2-1) was isolated by vacuum filtration and washed with cold water before being dried under vacuum at 24° C. If necessary, the product was purified by "Biotage" flash chromatography using 50:50 Hexanes:Ethyl Acetate with 1% triethylamine. The same acylation procedure is used to prepare Compounds 2-2 and 2-3 starting with the corresponding zwitterion 2b and 2c, respectively.

3-(S)-Phenoxyacetamido-2-(R)-[trans-2-(2-furanyl)ethylene]-4-oxo-1-azetidine Acetic Acid (Compound 2-1)

Isolated Yield=48% (96% of theory); m.p.=165–167° C.; IR (KBr cm$^{-1}$): 1676, 1738, 1768, 3293. $^1$H NMR (DMSO-d6) δ: 9.02 (1H, d), 7.66 (1H, s), 7.12 (2H, m), 6.84 (3H, m), 6.46 (3H, m), 6.12 (1H, dd), 5.24 (1H, dd, J=5.1 Hz), 4.54 (3H, m), 4.06 (1H, d), 3.74 (1H, d). $^{13}$C NMR (DMSO-d6) δ: 59.38, 60.79, 66.46, 109.49, 111.71, 114.48, 120.93, 121.91, 124.23, 129.24, 143.10, 151.49, 157.66, 166.07, 168.16, 169.39. MS (EI): m/e 371.1 (FW 370.1). Optical rotation: $[\alpha]_D$=63.66 (c 2, DMSO, 25° C.). e.e=100% Absolute configuration: (2R, 3S).

3-(S)-Phenoxyacetamido-2-(R)-(trans-2-phenylethylene)-4-oxo-1-azetidine Acetic Acid (Compound 2-2)

Isolated Yield=37% (74% of theory); m.p.=173–175° C.; IR (KBr cm$^{-1}$): 1656, 1729, 1778, 3283. $^1$H NMR (DMSO-d6) δ: 8.98 (1H, d), 7.42 (5H, m), 7.04 (2H, m), 6.86 (3H, m), 6.74 (1H, d), 6.40 (1H, dd), 5.34 (1H, dd, J=4.8 Hz), 4.54 (3H, m), 4.06 (1H, d), 3.74 (1H, d). $^{13}$C NMR (DMSO-d6) δ: 41.71, 59.26, 60.81, 66.46, 114.45, 120.96, 124.39, 126.60, 128.03, 128.62, 129.24, 135.64, 136.14, 157.66, 166.20, 168.12, 169.49. MS (EI): m/e 381.3 (FW 380.4). Optical rotation: $[\alpha]_D$=51.47 (c 2, DMSO, 25° C.). e.e=>98% Absolute configuration: (2R, 3S).

3-(S)-Phenoxyacetamido-2-(R)-[trans-2-(2-methoxyphenyl)ethylene]-4-oxo-1-azetidine Acetic Acid (Compound 2-3)

Isolated Yield=34% (68% of theory); m.p.=128–132° C.; IR (KBr cm$^{-1}$): 1680, 1729, 1753, 3314. $^1$H NMR (DMSO-d6) δ: 8.98 (1H, d), 7.46 (1H, d), 7.26 (2H, m), 7.06 (2H, m), 6.92 (5H, m), 6.36 (1H, dd), 5.30 (1H, dd, J=4.9 Hz), 4.56 (3H, m), 4.06 (1H, d), 3.78 (3H, s), 3.74 (1H, d). $^{13}$C NMR (DMSO-d6) δ: 41.67, 55.73, 59.27, 61.34, 64.44, 66.43, 111.36, 114.45, 120.49, 120.90, 124.73, 126.56, 129.23, 129.39, 130.26, 156.32, 157.66, 166.18, 168.08, 169.48. MS (EI): m/e 411.2 (FW 410.4). Optical rotation: $[\alpha]_D$=26.81 (c 2, DMSO, 25° C.). e.e=>95% Absolute configuration: (2R, 3S).

Example 3

Preparation of Compounds (3):

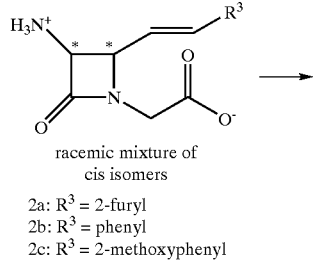

racemic mixture of cis isomers

2a: R$^3$ = 2-furyl
2b: R$^3$ = phenyl
2c: R$^3$ = 2-methoxyphenyl

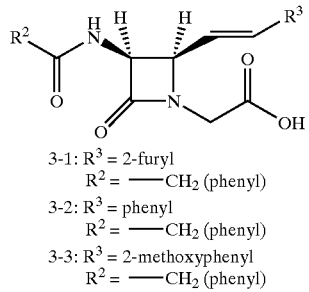

3-1: R$^3$ = 2-furyl
    R$^2$ = ——CH$_2$ (phenyl)
3-2: R$^3$ = phenyl
    R$^2$ = ——CH$_2$ (phenyl)
3-3: R$^3$ = 2-methoxyphenyl
    R$^2$ = ——CH$_2$ (phenyl)

Each of the compounds 3-1, 3-2, and 3-3 were prepared using the same procedures as described in Example 2 except using methyl phenylacetate instead of methyl phenoxyacetate and the corresponding zwitterion 2a, 2b or 2c.

3-(S)-Phenylacetamido-2-(R)-[trans-2-(2-furanyl)ethylene]-4-oxo-1-azetidine Acetic Acid (Compound 3-1)

Isolated Yield=35% (70% of theory); m.p.=200–201° C.; IR (KBr cm$^{-1}$): 1653, 1732, 1769, 3289. $^1$H NMR (DMSO-d6) δ: 8.92 (1H, d), 7.64 (1H, br), 7.08 (5H, m), 6.44 (2H, m), 6.36 (1H, d), 6.00 (1H, dd), 5.12 (1H, q, J=5.01 Hz), 4.42 (1H, q), 3.86 (1H, d), 3.38 (4H, m). $^{13}$C NMR (DMSO-d6) δ: 42.07, 42.98, 59.78, 60.33, 109.30, 111.74, 122.58, 123.73, 126.27, 128.05, 128.87, 136.04, 143.10, 151.68, 166.21, 169.89, 170.44. MS (EI): m/e 353.4 (FW 354.4). Optical rotation: $[\alpha]_D$=138.97 (c 2, DMSO, 25° C.). e.e=100% Absolute configuration: (2R, 3S).

3-(S)-Phenylacetamido-2-(R)-(trans-2-phenylethylene)-4-oxo-1-azetidine Acetic Acid (Compound 3-2)

Isolated Yield=33% (66% of theory); m.p.=179–184° C.; IR (KBr cm$^{-1}$): 1661, 1735, 1774, 3293. $^1$H NMR (DMSO-d6) δ: 8.98 (1H, d), 7.40 (5H, m), 7.08 (5H, m), 6.64 (1H, d), 6.32 (1H, d), 5.28 (1H, dd, J=4.8 Hz), 4.50 (1H, dd), 4.06 (1H, d), 3.82 (1H, d), 3.44 (2H, m). $^{13}$C NMR (DMSO-d6) δ: 41.76, 42.01, 59.68, 60.78, 124.43, 126.21, 126.32, 127.99, 128.57, 128.78, 135.39, 135.89, 136.10, 166.53, 169.49, 170.38. MS (EI): m/e 363.3 (FW 364.3). Optical rotation: $[\alpha]_D$=114.89 (c 2, DMSO, 25° C.). e.e=>98% Absolute configuration: (2R, 3S).

3-(S)-Phenylacetamido-2-(R)-[trans-2-(2-methoxyphenyl)ethylene]-4-oxo-1-azetidine Acetic Acid (Compound 3-3)

Isolated Yield=28% (56% of theory); m.p.=159–165° C.; IR (KBr cm$^{-1}$): 1653, 1739, 1765, 3287. $^1$H NMR (DMSO-d6) δ: 8.98. (1H, d), 7.42 (1H, d), 7.26 (1H, m), 7.16 (2H, m), 7.04 (5H, m), 6.88 (1H, d), 6.36 (1H, dd), 5.36 (1H, dd, J=4.9 Hz), 4.50 (1H, dd), 4.04 (1H, d), 3.78 (4H, m), 3.44 (2H, m). $^{13}$C NMR (DMSO-d6) δ: 41.38, 41.99, 55.74, 59.76, 61.31, 111.34, 120.45, 124.54, 124.67, 126.21, 126.66, 127.98, 128.98, 129.35, 129.96, 135.88, 156.28, 166.51, 169.50, 170.34. MS (EI): m/e 393.2 (FW 394.4). Optical rotation: $[\alpha]_D$=71.43 (c 2, DMSO, 25° C.). e.e=>95% Absolute configuration: (2R, 3S).

Example 4

Example 4 demonstrates the derivatization of the unsaturated side chain.

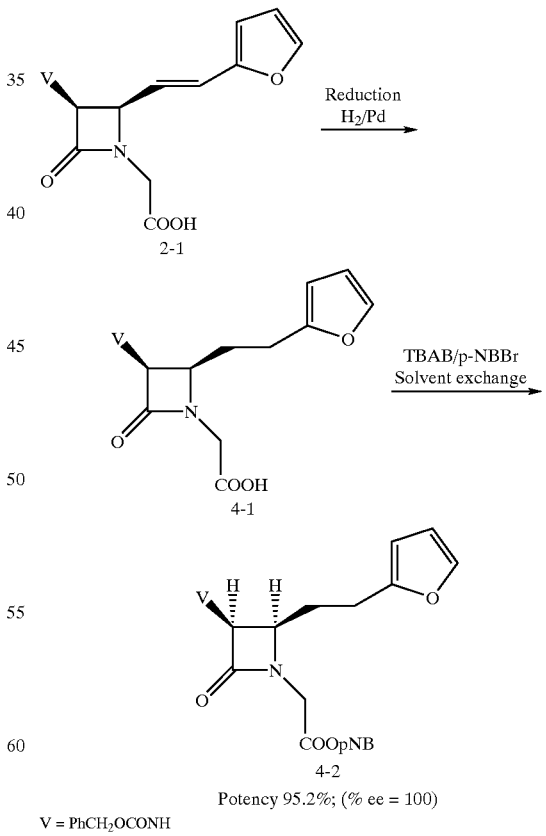

V = PhCH$_2$OCONH

Compound 4-2 was prepared by reduction of the double bond of Compound 2-1 with Pd/C catalyst under a hydrogen atmosphere using standard hydrogenation procedures to produce Compound 4-1 followed by esterification of the acid with p-nitrobenzyl bromide (p-NBBr) in the presence of tetrabutyl ammonium bromide (TBAB). (see, e.g., Doecke, C. W, et al., *Synthesis*, 11, 985–988 (1991).)

Preparation of 3-(S)-Phenoxyacetamido-2-(R)-[2-(2-furanyl)ethyl]-4-oxo-1-azetidine Acetic Acid (4-1)

The filtered enzymatic acylation reaction solution was charged to a 1 liter 3-necked round bottom flask equipped with an overhead stirrer. To this solution was added 80 ml of methylene chloride. The pH was adjusted to 2.0–2.3 with 37% hydrochloric acid and stirred for 5 minutes. The layers were separated, keeping any emulsion with the lower organic layer. The upper aqueous layer was extracted with 30 ml of methylene chloride. The layers were separated and the organic layers combined. The aqueous layer was discarded. The combined organic layer was dried over anhydrous $Na_2SO_4$ and concentrated at reduced pressure and +25° C. to approximately 100 ml volume. This solution was slowly added to Parr shaker bottle containing 10 mol % palladium on carbon (5%) and the mixture shaken under 40 psi hydrogen gas at room temperature for about 4 hours. After 4 hours, TLC analysis indicated a complete reaction by the absence of starting material so the reaction mixture was vacuum filtered through celite and the solids rinsed with a minimum of $CH_2Cl_2$. An aliquot of the filtrate was concentrated to dryness and analyzed by $^1H$ NMR for complete reduction (disappearance of double bond proton resonance).

M.p.=160–162° C.; $^1H$ NMR (DMSO-d6) δ: 9.10 (1H, d), 7.48 (1H, d), 7.22 (2H, m), 6.94 (3H, m), 6.32 (1H, m), 6.04 (1H, m), 5.10 (1H, dd, J=5.1 Hz), 4.58 (2H, s), 3.94 (1H, m), 3.72 (1H, d), 3.28 (1H, d), 2.46 (2H, m), 1.92 (1H, m), 1.70 (1H, m).

Preparation of 3-(S)-Phenoxyacetamido-2-(R)-[2-(2-furanyl)ethyl]-4-oxo-1-azetidine Acetic Acid, p-Nitrobenzyl Ester (4-2)

The reduction filtrate in $CH_2Cl_2$ from above and DI water (50:50) were charged to a three necked round bottomed flask, equipped with an overhead stirrer, and with slight agitation, the pH was adjusted to 7.5 to 7.8. This was stirred for 5 minutes to ensure a stable pH. To this mixture was added tetrabutylammonium bromide (0.005 mol) and p-nitrobenzyl bromide solution (0.08 mol). If necessary, the reaction pH was readjusted to 7.5 to 7.8. The mixture was then heated to reflux with a heating mantle and stirred for 6 hours. After refluxing, the reaction was allowed to cool overnight without agitation. The layers were separated, keeping any emulsion with the lower organic layer, and the upper aqueous layer discarded.

The organic layer was charged to a 1-liter 4-necked round bottom flask equipped with an overhead stirrer, heating mantle, thermometer, addition funnel, and a Barrett style distilling adapter with cold water condenser. The methylene chloride was slowly distilled off while adding 213 ml of methyl alcohol. The rate of MeOH addition was slightly faster than the rate of $CH_2Cl_2$ distillation. The heat was removed when the mixture reached 62° C. and it was slowly cooled and stirred for 2 hours at room temperature. The product (4-2) was vacuum filtered and washed with 100 ml of room temperature methyl alcohol before drying under vacuum (25–30 inches of mercury) at 30–35° C. at overnight.

M.p.=130–131° C.; $^1H$ NMR (CDCl$_3$) δ: 8.22 (2H, d), 7.50 (2H, d), 7.28 (4H, m), 7.12 (1H, d), 7.02 (1H, m), 6.90 (2H, m), 6.22 (1H, m), 5.94 (1H, m), 5.40 (1H, dd, J=5.1 Hz), 5.26 (1H, s), 4.56 (1H, s), 4.24 (1H, d), 4.04 (1H, m), 3.80 (1H, d), 2.58 (2H, m), 1.94 (1H, m), 1.72 (1H, m).

We claim:

1. A process for preparing a cis-β-lactam having structure II

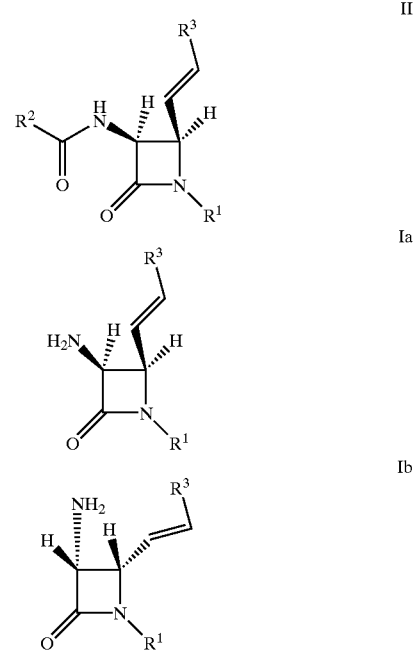

where $R^1$ is $-SO_3(C_1-C_4)$alkyl, $-CH_2CO_2H$, or $-CH_2CO_2R^{1'}$, where $R^{1'}$ is $(C_1-C_4)$alkyl, benzyl, or p-nitrophenylmethylene; $R^2$ is benzyl or phenoxymethylene; and $R^3$ is 2-furyl, phenyl, or 2-methoxyphenyl comprising the steps of (i) providing a racemic mixture of cis-azetidinones having structures Ia and Ib where $R^1$ is $-SO_3(C_1-C_4)$alkyl, $-CH_2CO_2H$, or $-CH_2CO_2R^{1'}$, where $R^1$ is $(C_1-C_4)$ alkyl, benzyl, or p-nitrophenylmethylene and $R^3$ is 2-furyl, phenyl, or 2-methoxyphenyl; and (ii) reacting said racemic mixture with a $(C_1-C_4)$alkyl phenylacetate or a $(C_1-C_4)$alkyl phenoxyacetate in the presence of penicillin G amidase.

2. A process for preparing a cis-β-lactam having structure III

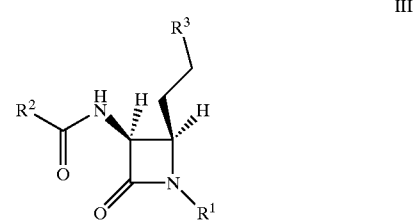

where $R^1$ is $-SO_3(C_1-C_4)$alkyl, $-CH_2CO_2H$, or $-CH_2CO_2R^{1'}$, where $R^1$ is $(C_1-C_4)$alkyl, benzyl, or p-nitrophenylmethylene; $R^2$ is benzyl or phenoxymethylene; and $R^3$ is 2-furyl, phenyl, or 2-methoxyphenyl comprising the steps of (i) providing a racemic mixture of cis-azetidinones having structures Ia and Ib

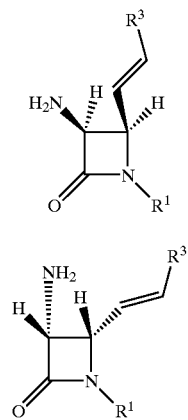

where $R^1$ is $—SO_3(C_1–C_4)$alkyl, $—CH_2CO_2H$, or $—CH_2CO_2R^{1'}$, where $R^{1'}$ is $(C_1–C_4)$alkyl, benzyl, or p-nitrophenylmethylene; and $R^3$ is 2-furyl, phenyl, or 2-methoxyphenyl; and (ii) reacting said racemic mixture with a $(C_1–C_4)$alkyl phenylacetate or a $(C_1–C_4)$alkyl phenoxyacetate in the presence of penicillin G amidase to produce a cis-β-lactam having structure II

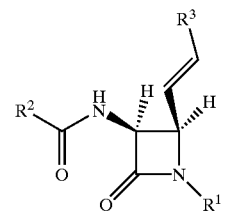

where $R^1$ is $—SO_3(C_1–C_4)$alkyl, $—CH_2CO_2H$, or $—CH_2CO_2R^{1'}$, where $R^{1'}$ is $(C_1–C_4)$alkyl, benzyl, or p-nitrophenylmethylene; $R^2$ is benzyl or phenoxymethylene; and $R^3$ is 2-furyl, phenyl, or 2-methoxyphenyl; and (iii) hydrogenating said cis-β-lactam having structure II to produce said cis-β-lactam having structure III.

3. The process of claim 2 wherein $R^1$ is $—CH_2CO_2H$, or $—CH_2CO_2R^{1'}$.

4. The process of claim 3 wherein $R^3$ is 2-furyl.

* * * * *